US009925311B2

United States Patent
Grunwald et al.

(10) Patent No.: US 9,925,311 B2
(45) Date of Patent: Mar. 27, 2018

(54) KIT FOR PRODUCING A CROSSLINKED GEL FOR SURROUNDING URINARY CALCULI AND/OR FRAGMENTS THEREOF

(71) Applicants: FRAUNHOFER-GESELLSCHAFT ZUR FÖRDERUNG DER ANGEWANDTEN FORSCHUNG E.V., München (DE); ALBERT-LUDWIGS-UNIVERSITÄT FREIBURG, Freiburg (DE)

(72) Inventors: Ingo Grunwald, Lilienthal (DE); Katharina Richter, Bremen (DE); Arkadiusz Miernik, Freiburg (DE); Martin Schoenthaler, Freiburg (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 14/786,807

(22) PCT Filed: Aug. 22, 2013

(86) PCT No.: PCT/EP2013/067438
§ 371 (c)(1),
(2) Date: Oct. 23, 2015

(87) PCT Pub. No.: WO2014/173468
PCT Pub. Date: Oct. 30, 2014

(65) Prior Publication Data
US 2016/0074561 A1 Mar. 17, 2016

(30) Foreign Application Priority Data
Apr. 23, 2013 (EP) ..................... 13164960

(51) Int. Cl.
| A61B 17/22 | (2006.01) |
| A61L 31/02 | (2006.01) |
| A61L 31/04 | (2006.01) |
| A61L 31/14 | (2006.01) |
| A61B 17/00 | (2006.01) |
| A61B 17/221 | (2006.01) |

(52) U.S. Cl.
CPC .......... *A61L 31/022* (2013.01); *A61L 31/042* (2013.01); *A61L 31/14* (2013.01); *A61L 31/145* (2013.01); *A61B 17/22* (2013.01); *A61B 17/221* (2013.01); *A61B 2017/00876* (2013.01); *A61L 2300/102* (2013.01); *A61L 2400/06* (2013.01)

(58) Field of Classification Search
CPC ...... A61L 31/022; A61L 31/042; A61L 31/14; A61L 31/145; A61L 2300/102; A61L 2400/06; C08L 5/04; C08L 5/06; A61B 17/221; A61B 2017/00876; A61B 17/22
See application file for complete search history.

(56) References Cited

U.S. PATENT DOCUMENTS

| 5,244,913 A | 9/1993 | Coulter et al. |
| 6,544,227 B2 | 4/2003 | Sahatjian et al. |
| 6,663,594 B2 | 12/2003 | Sahatjian et al. |
| 2002/0119116 A1* | 8/2002 | Sahatjian ......... A61B 17/22012 424/78.31 |
| 2003/0100752 A1* | 5/2003 | Robinson ......... A61K 47/48069 540/145 |
| 2006/0269512 A1 | 11/2006 | McDougal et al. |
| 2007/0231393 A1 | 10/2007 | Ritter et al. |
| 2008/0065012 A1 | 3/2008 | Hebert et al. |
| 2008/0103481 A1* | 5/2008 | Vogel ............... A61B 17/12022 604/514 |
| 2009/0136594 A1 | 5/2009 | McLeroy et al. |
| 2009/0162411 A1 | 6/2009 | Buensuceso et al. |
| 2010/0121188 A1* | 5/2010 | Sandhu .................... A61F 2/01 600/435 |
| 2011/0097367 A1 | 4/2011 | Wallrapp et al. |
| 2012/0108676 A1 | 5/2012 | Smyth et al. |

FOREIGN PATENT DOCUMENTS

| CA | 2710986 A1 | 7/2009 |
| CN | 101700422 A | 5/2010 |

(Continued)

OTHER PUBLICATIONS

Le Renard et al., "The in vivo performance of magnetic particle-loaded injectable, in situ gelling, carriers for the delivery of local hyperthermia," *Biomaterials* 31:691-705, 2010.

(Continued)

*Primary Examiner* — Richard Louis
(74) *Attorney, Agent, or Firm* — Seed IP Law Group LLP

(57) ABSTRACT

Described is a kit for producing a crosslinked gel for surrounding urinary calculi and/or fragments thereof, more particularly kidney stones and/or fragments thereof, comprising a composition (A) comprising one or several cationically crosslinkable polymer(s), and a composition (B) comprising one or several crosslinking agent(s) for crosslinking the cationically crosslinkable polymer(s), wherein composition (A) and/or composition (B) additionally comprise(s) magnetizable particles or the kit additionally comprises a composition (C) that contains magnetizable particles. Upon contact of composition (A) with composition (B) in a region of the urinary tract, more particularly the kidney, that contains urinary calculi and/or fragments thereof, more particularly kidney stones and/or fragments thereof, a crosslinked gel is formed that partly or fully surrounds the urinary calculi and/or fragments thereof, more particularly kidney stones and/or fragments thereof, and that contains the magnetizable particles. The gel together with the urinary calculi and/or fragments thereof, more particularly kidney stones and/or fragments thereof, can then be removed from the body by using magnetic interactions.

17 Claims, No Drawings

(56) References Cited

FOREIGN PATENT DOCUMENTS

| JP | 2004524898 A | 8/2004 |
|---|---|---|
| JP | 2010-510814 A | 4/2010 |
| WO | 98/12228 A1 | 3/1998 |
| WO | 01/05443 A1 | 1/2001 |
| WO | 02/18448 A2 | 3/2002 |
| WO | 02067788 A1 | 9/2002 |
| WO | 2004/080343 A2 | 9/2004 |
| WO | 2005/037062 A2 | 4/2005 |
| WO | 2008042756 A1 | 4/2008 |
| WO | 2008/103891 A2 | 8/2008 |
| WO | 2009/070766 A2 | 6/2009 |

OTHER PUBLICATIONS

Tan et al., "In Vitro Comparison of Prototype Magnetic Tool with Conventional Nitinol Basket for Ureteroscopic Retrieval of Stone Fragments Rendered Paramagnetic with Iron Oxide Microparticles," *The Journal of Urology* 188:648-652, 2012.

Geppert et al., "Uptake of dimercaptosuccinate-coated magnetic iron oxide nanoparticles by cultured brain astrocytes," Nanotechnology, 22(14): 10 pages, Feb. 24, 2011.

Cha et al., "Bulk adhesive strength of recombinant hybrid mussel adhesive protein," Biofouling 25(2):99-107, Feb. 2009.

Leung et al., "Characteristics and Properties of Carboxylated Cellulose Nanocrystals Prepared from a Novel One-Step Procedure," small 7(3):302-305, 2011.

\* cited by examiner

KIT FOR PRODUCING A CROSSLINKED GEL FOR SURROUNDING URINARY CALCULI AND/OR FRAGMENTS THEREOF

BACKGROUND

Technical Field

The present invention primarily relates to a kit for producing a crosslinked gel, more particularly an adhesive, comprising magnetizable particles for partly or fully surrounding urinary calculi and/or fragments thereof, more particularly kidney stones and/or fragments thereof, in the body, more particularly in the urinary tract.

More particularly the present invention relates to a kit comprising a composition (A) comprising one or several cationically crosslinkable polymer(s), and a composition (B) comprising one or several crosslinking agent(s) for crosslinking the cationically crosslinkable polymer(s), wherein composition (A) and/or composition (B) additionally comprise(s) magnetizable particles or the kit additionally comprises a composition (C) that contains magnetizable particles. Upon contact of composition (A) with composition (B) in a region of the urinary tract, more particularly the kidney, that contains urinary calculi and/or fragments thereof, more particularly kidney stones and/or fragments thereof, a crosslinked gel is formed that partly or fully surrounds the urinary calculi and/or fragments thereof, more particularly kidney stones and/or fragments thereof, and that contains the magnetizable particles. Using magnetic interactions, the gel together with the urinary calculi and/or fragments thereof, more particularly kidney stones and/or fragments thereof, can be removed from the body, more particularly from the urinary tract.

Description Of The Related Art

Urinary calculi can be formed in the revulsive urinary tract. A urinary obstruction first leads to strong, labor-like pain (so called renal colic). If left untreated, urinary calculi can lead to serious health problems (loss of renal function, inflammation) and vitally endanger the patient (sepsis during infected urinary calculus-caused urinary transport disorder). From an epidemiological point of view, urinary calculus conditions are one of the most prevalent diseases afflicting mankind, whose incidence in Germany amounted to 1.45% in the year 2000, which in turn corresponds to 1.200.000 new cases per year. In Germany alone a total of ca. 750.000 cases of treatment can be expected per year.

The number of treatments for removing calculi in Germany is estimated to be about 400.000 per year, about half thereof being treatments of recurring calculi. The numbers referred to can be extrapolated to a millionfold implementation of such treatments worldwide. With a sum of over 1.5 billion Euros, urinary calculus conditions represent a substantial cost factor for the German healthcare sector.

If the calculi do not exit the body by natural routes or if medicinal indications for immediate therapy exist, endoscopy (minimally invasive endoscopy techniques) represents the therapeutic "gold standard" besides the extracorporeal shock wave treatment (ESWT). In light of increasing evidence for worse results of ESWT, endoscopic methods are preferably used. It can be assumed that currently 60-70% of calculi patients are treated endoscopically. This tendency is increasing. With the help of endoscopic techniques, calculi are locally crushed and removed. To date, small residual fragments (<2 mm), that cannot be removed effectively during treatment, pose an unsolved problem. Remaining fragments of kidney stones act as "crystal seeds" from which new calculi are formed with a likelihood of 70%. This in turn leads again to medicinal problems and need for treatment.

About 30 million people in Europe are suffering from kidney stones (ca. 5% of the population), and the frequency of occurrence of urinary calculi conditions shows an increasing tendency in industrialized countries. The risk to be repeatedly affected by kidney stones after recovery is particularly high (ca. 60%). Medicinal complications that can arise in connection with kidney stones are loss of renal function and infectious complications all the way to sepsis. This results in a severe burden for the healthcare systems.

One option to specifically navigate the position and distribution of substances or objects in the body is the utilization of magnetic interactions. For this purpose, the target substances and target objects, respectively, have to be magnetized accordingly. Magnetic (nano)particles have already proven to be suitable in different biomedical applications, since they have high biocompatibility and can be modified with different functional groups. Thus, magnetic particles are used, for example, to transport active substances to a desired site of action in the body. Hence, therapeutic and diagnostic substances can be used efficiently and damages in healthy tissues caused by potential side effects can be minimized. In this context, US 2007/0231393 describes a method in which magnetic drug carrier particles are positioned in the body by means of an external magnetic field.

US 2009/0136594 is concerned with a method to magnetize biological particles by contacting them with magnetic particles which are modified such that they are able to bind specifically to the biological particles. Kidney stones and fragments thereof can be magnetized as one possible application to remove them from the body by means of equipment that magnetically attracts such particles. In order to specifically bind calcium-based biominerals (such as, for example, kidney stones), the particles are modified with certain calcium-binding proteins or fragments thereof.

Larger calculi usually cannot be removed by means of a minimally invasive procedure and therefore have to be smashed into smaller fragments first and have to be dissolved completely or at least partly, respectively. A method for treatment of kidney stones through specific dissolution of the deposits by using quaternary ammonium salts is described, for example, in U.S. Pat. No. 5,244,913.

Another possibility for treating kidney stones without smashing them beforehand is specified in US 2006/0269512. Here, the natural peristalsis is used to press a polymer clot through a lumen and to thereby remove the calculus from the lumen. The polymer clot can be formed in situ through temperature or pH change or through ionic interactions.

Lithotripsy is a method where kidney stones are smashed by means of extracorporeal shock waves or endoscopically inserted laser or compressed air probes. Thereby, fragments of different sizes are formed which can be removed with the aid of grasping instruments or can be flushed out. One problem occurring during lithotripsy is that the fragments spread during smashing and can thereby damage surrounding tissue or reach regions that are hard to access.

WO 2005/037062 relates to a method in which kidney stones are enclosed (not enclosed in) in a certain area with the aid of a polymer clot, whereby damages to the tissues through the formed fragments during smashing can be prevented to a large extent. According to WO 2005/037062, a gel-forming liquid, for example a thermosensitive polymer, is injected into the lumen on at least one side of the kidney stone, which forms a gel clot at body temperature. The polymer thereby usually does not get into contact with the kidney stone, but serves to increase the efficiency of the lithotripsy by preventing shifting of the kidney stone and by protecting the surrounding tissue from damage through fragmentation.

According to US 2008/0103481, a biocompatible polymer clot is used more particularly to prevent a backwards shift of kidney stones or fragments thereof during lithotripsy and thereby to minimize the damage to the surrounding tissues.

An approach to remove objects, such as for example blood clots, from the body using an adhesive is specified in US 2008/0065012. In the process, the adhesive is distributed on a surface and inserted into the body with the aid of a catheter. When the object is adhered to the surface, the catheter is removed and takes the object with it.

Adhesives based on biological macromolecules and more particularly gel-forming polymer systems are used increasingly in medical technology. Thereby, their high biocompatibility is one of their most important selection criteria.

Thermosensitive or ionically polymerizable polymers are used, for example, to stop the blood flow from injured blood vessels. WO 2008/103891 specifies a method in which the outflow of biological fluids from tissues or vessels can be controlled through in situ formation of a polymer clot.

WO 01/05443 relates to an adhesive protein foam and its use for surgical and therapeutic applications. The foam consists of a liquid protein matrix and a biocompatible gas and serves for covering and protecting, respectively, injured tissue or for connecting implanted tissue with biological tissue.

WO 02/18448 describes the pharmaceutical use of percarboxylated polysaccharides in the manufacture of biomaterials for surgical and biomedical applications. Such material are especially well suited for use in the body since they are recognized as being endogenous and do not trigger any immune rejection reaction. Therefore, they can be used as coatings for implants.

A method for encapsulation of renal tissue in spheres of biocompatible polymers is described in US 2009/0162411. The aim of such encapsulation is to maintain renal tissue implants, which can be injected into a patient who suffers from a renal function disorder in order to support renal function.

Calcium alginate as a biocompatible hydrogel polymer for closing skull openings after open brain surgery is disclosed in WO 2004/080343.

The suitability of polysaccharide-containing polymers for binding biologically active molecules or whole cells in the field of organ transplantation and of artificial tissue replacement is described in WO 1998/012228.

Alginates are also used as fillers for supporting skin and muscles in the medicinal and cosmetic field. In US 2011/0097367 applications are described in which monolithic alginate implants are formed in situ by means of injection of a pure, high molecular weight alginate solution into the tissue and spontaneous crosslinking Crosslinking takes place through $Ca^{2+}$ ionic bridges without the need of having to add additional crosslinking agents. The described alginate implants are suitable for the treatment of wrinkles or different conditions in which the muscular structure is weakened.

In U.S. Pat. No. 6,663,594 B2, a method for immobilization of an object in the body, for example a kidney stone, is described, wherein a gel-forming liquid is injected into the body. Upon contact with the object, a gel is formed, which at least partly captures and immobilizes the object. The immobilization serves for being able to subsequently fragment the object without risking distribution of the fragments and for removing the object or fragments, respectively, from the body with an endoscopic tool. The gel thereby prevents the object or fragment, respectively, from shifting and not being able to be grasped with the tool. After removal of the object or fragments, respectively, the gel is dissolved or extracted with the aid of an endoscopic tool. A disadvantage of the method is that during smashing of the kidney stones the gel that is already set might be destroyed and thereby fragments can be released again or that discrete fragments might escape from the polymer. In addition, the described procedure is very time-consuming, since the calculi or fragments thereof have to be grasped and removed individually. Consequently, individual calculus fragments will remain behind with a relatively high likelihood.

More particularly, one problem of lithotripsy is the occurrence of medium sized calculus fragments (more particularly <2 mm), also called "gravel", since these fragments can neither be grasped efficiently nor flushed. Residual fragments of this size slide through the mesh of the grasping instruments (grasping forceps or baskets) and render the extraction of gravel very time-consuming and with larger amounts of calculi practically unfeasible. To date, no technology has been successfully established to fully remove the medium size and small calculus fragments. Such kidney stone fragments remaining behind, however, in a large percentage of cases lead to the formation of new kidney stones, since the fragments serve as "crystal seeds".

In order to ensure complete removal of fragments of any size, a simple method has to be developed which is suited to ideally reliably capture all of the fragments. Thereby, the problems and difficulties (partly mentioned above) that are entailed in the methods known in the state of the art, shall preferably be avoided.

BRIEF SUMMARY

The primary object of the present invention was to provide a kit that is used for being able to reliably extract urinary calculus fragments, in particular, from the body, preferably by means of a minimally invasive method.

Further objects of the present invention arise from the following description as well as, more particularly, from the attached patent claims.

The primary object is solved according to one aspect of the present invention by a kit for producing a crosslinked gel, more particularly an adhesive, for partly or fully surrounding urinary calculus fragments, more particularly kidney stone fragments, comprising (a) a composition (A) comprising one or several cationically crosslinkable polymer(s), and (b) a composition (B) comprising one or several crosslinking agent(s) for crosslinking the cationically crosslinkable polymer(s), wherein composition (A) and/or composition (B) additionally comprise(s) magnetizable particles or the kit additionally comprises a composition (C) that contains magnetizable particles.

Within the scope of the present invention, a region of the urinary tract or the kidney, respectively, is to be understood as meaning the pelvicocaliceal system, in particular, as well as the revulsive urinary paths, ureter, bladder or urethra.

"Urinary calculus fragments" are in connection with the present invention to be understood as meaning fragments of urinary calculi, more particularly kidney stones, that formed, in particular, by means of smashing urinary calculi (lithotripsy).

By means of embedding of the urinary calculi according to the invention and subsequent extraction of the "adhesive composite", preferably fragments of any size can be fully removed and thereby repeated calculus formation can be prevented.

The polymers or polymer units, respectively, of composition (A) are crosslinked via ionic interactions (see composition (B)). Therefore, a multitude of macromolecules that occur as ligands of monovalent or multivalent cations and are able to form chelate complexes are suitable for application according to the invention. These include more particularly hydrogels, biocompatible sugar-based (e.g., modified celluloses) or proteinogenic adhesives or fibrin-based or collagen-based systems (particularly preferred polymers are described below).

Polyphenolic proteins, for example, are able to set via crosslinks of their protein scaffold with the aid of a catechol oxidase. Such crosslinks can also be achieved in vitro, for example, with the aid of metal ions. The use of hybrid systems is also conceivable that are based on a combination of synthetic polymers with phenolic amino acids. The post-translational amino acid 3,4-dihydroxyphenylalanine (DOPA), for example, is specifically suited for polymer modification, because of its diverse possibilities for reaction with different functional groups, and corresponding gel systems are characterized by improved adhesive and cohesive properties.

Suitable cations preferably serve as crosslinking agents of composition (B). Advantageously, this usually concerns cations that naturally occur in physiological systems. Advantageously, no additional (aggressive) reagents have to be added to start the crosslinking reaction under physiological conditions. In addition, advantageously no undesired byproducts are formed.

Preferred according to the invention are such systems that are able to set under physiological conditions. In order to form stable crosslinks via cationic bridges, it is advantageous if the polymers of composition (A) have functional groups (in sufficient number) that are available as negatively charged units even at (slightly) acidic pH. In some systems, the degree of crosslinking or the speed of crosslinking, for example, can be controlled via influenceable factors such as concentration or pH-value.

According to a preferred embodiment composition (A) and/or composition (B) contain chitosan. Preferably, composition (B) contains chitosan.

Compositions (A) and (B) can be introduced one after the other or together, whereby it is preferred that composition (B) is introduced before composition (A) to guarantee a suitable distribution and complete embedding of all of the urinary calculus fragments, more particularly kidney stone fragments, before start of and during crosslinking, respectively.

The setting preferably occurs in a region of the urinary tract, more particularly the kidney, in which urinary calculi and/or fragments thereof, more particularly kidney stones and/or fragments thereof, more particularly of medium size (preferably with an average mean diameter of 0.1 to 4 mm, preferably of 0.2 to 3 mm, particularly preferably of 0.5 to 2 mm) are present, so that these can be fully or at least partly surrounded on site. The crosslinked gel according to the invention preferably sets under physiological conditions and has sufficient stability and flexibility to be extracted from the body preferably in one piece. The gel-calculus fragment-conglomerate(s) preferably has or have a diameter of 4 mm or less, respectively.

A system according to the invention can additionally contain further components. Substances, for example, that support the gel formation and/or embedding of the urinary calculus fragments, more particularly kidney stone fragments, can be added to compositions (A) and/or (B) and/or to one or several further compositions of a system according to the invention. Such substances may be, e.g., crosslinkers for increasing the stability of the gel.

According to a preferred embodiment of the present invention, the or one, several or all of the cationically crosslinkable polymer(s), respectively, of composition (A) is or are selected from the group consisting of polysaccharides, more particularly polysaccharides with deprotonated or deprotonatable functional groups, preferably carboxy groups, preferably polysaccharides from the group of polyuronides, particularly preferred polysaccharides from the group of alginates and pectins.

Polysaccharides such as alginates and pectins are particularly suited for use in the body, since they do not trigger any inflammatory reactions or immune rejection and involve a minimal risk of tissue trauma. Additionally, they are biodegradable and have a large amount of carboxylic acid groups that are able to form chelate complexes with multivalent cations. Advantageously, they are able to crosslink under water and at physiological temperatures and can be handled easily in solution. The crosslinking thereby takes place quickly but without agglutinating delicate renal tubules or the endoscopy instruments. The formed gels exhibit sufficient stability and flexibility to be extracted together with the urinary calculus fragments.

According to a further preferred embodiment of the present invention, the or one, several or all of the crosslinking agent(s), respectively, of composition (B) is/are selected from the group consisting of divalent and trivalent cations, preferably iron and calcium ions.

Iron and calcium ions are cations that occur naturally in physiological systems and that can be easily administered in the form of biologically compatible solutions. They have a suitable coordination chemistry and are able to form stable chelate complexes for crosslinking.

According to a further preferred embodiment of the present invention, composition (B) has an acidic pH-value, preferably a pH in the range of 3.5 to 4.5.

At a pH in the range of 3.5 to 4.5 the cations exist freely in solution and are therefore available for complexation. Advantageously, in this pH range the acid groups that are located at the polysaccharide are deprotonated to a large extent, whereby an effective crosslinking reaction takes place. If a buffered solution (at a pH of approx. 4) is provided in the region of the urinary calculus fragments, more particularly kidney stone fragments, that are to be removed, the introduction of the polysaccharide-containing composition (A) leads to a reduction of the solubility (coacervation). The process of coacervation takes a certain amount of time while the urinary calculus fragments are embedded. Advantageously, the speed of the crosslinking reaction is thereby also controllable via the pH of the used compositions.

According to a further preferred embodiment of the present invention, the magnetizable particles are selected from particles comprising or consisting of ferromagnetic elements such as iron, nickel and cobalt as well as alloys such as AlNiCo, SmCo, $Nd_2Fe_{14}B$, $Ni_{80}Fe_{20}$, NiFeCo and/ or oxides thereof such as iron oxide particles, more particularly iron oxide nanoparticles made of $Fe_3O_4$ and/or $\gamma\text{-}Fe_2O_3$.

The addition of magnetizable particles opens up an advantageous method to remove the set "adhesive composite" from the body by utilizing the magnetic properties. A magnet fishing instrument or more particularly a magnetic retrieval basket can be used for instance, which combines the advantages of an anchor and of a usual retrieval basket.

Iron oxide particles haven proven to be suitable for medical technology and pharmaceutical applications, e.g., as intravenously administered contrast agents for magnetic resonance imaging or for tumor therapy. To increase the biocompatibility and colloidal stability, such particles are usually coated with, e.g., dextranes, polyvinyl alcohols, dimercapto succinic acid and others.

Moreover, the iron oxide particles provide a dark color to the adhesive, which enables a simpler handling according to visual aspects in contrast to the unmodified gel which is almost colorless.

According to a preferred embodiment of the present invention, the total amount of the magnetizable particles with regard to the total weight of composition (A) or (B) or (C), respectively, that contains the magnetizable particles, is at least 0.1 wt.-% and is preferably in the range of 0.1 to 70 wt.-%, particularly preferably in the range of 1 to 11 wt.-%.

In order to guarantee that the gel comprising the urinary calculi and/or fragments thereof, more particularly kidney stones and/or fragments thereof, can be efficiently removed from the body by using magnetic interactions, it is necessary to use a suitable amount of magnetizable particles in the crosslinked gel.

According to a preferred embodiment of the present invention, the concentration of the crosslinking agents that are comprised in composition (B) is at least 0.1 mol/L and preferably is in the range of 0.1 to 3 mol/L, particularly preferably in the range of 0.1 to 1 mol/L, with regard to the total volume of composition (B).

The amount of crosslinking agent present influences the speed of the crosslinking reaction as well as the stability and flexibility of the crosslinked gel. The amounts stated in the preferred embodiment of the present invention described above guarantee that a stable and flexible gel, which can be removed from the body in one piece if applicable, is formed as fast as possible.

In a further preferred embodiment, the total amount of chitosan present in composition (A) and/or in composition (B) is between 0.05 wt.-% and 1 wt.-% with regard to the total weight of composition (A) or (B), respectively.

According to a further preferred embodiment of the present invention, composition (A), composition (B), composition (C) if applicable or a further composition (D) comprised in the kit if applicable, comprises one or several substances for improving the crosslinking of the cationically crosslinkable polymer(s), more particularly crosslinkers. Compounds with functional groups from which he can select the ones that are suitable for improving the crosslinking are known to the person skilled in the art. Amino acids can be used for instance.

An addition of substances that improve the crosslinking of the gel ensures that the urinary calculi and/or fragments thereof, more particularly kidney stones and/or fragments thereof, are securely surrounded and that the gel won't rupture during the process of extraction. This enables a complete removal of all of the urinary calculi and/or fragments thereof, more particularly kidney stones and/or fragments thereof, in one extraction step.

According to a further preferred embodiment of the present invention, composition (A), composition (B), composition (C) if applicable or a further composition (D) or (E) comprised in the kit if applicable, comprises one or several substances for improving or enabling the formation of covalent bonds between the crosslinked gel and the urinary calculus fragments, more particularly kidney stone fragments, that are to be surrounded.

Substances that improve or enable the formation of covalent bonds between the crosslinked gel and the urinary calculi and/or fragments thereof, more particularly kidney stones and/or fragments thereof, that are to be surrounded, ensure that also urinary calculi and/or fragments thereof, more particularly kidney stones and/or fragments thereof, which possibly were not fully surrounded by or only got in contact with the crosslinked gel, are securely captured and also extracted.

According to a further preferred embodiment of the present invention, composition (A), composition (B), composition (C) if applicable or a further composition (D), (E) or (F) comprised in the kit if applicable, comprises one or several further substances from the following list: dyes, contrast agents, preservatives and stabilizers.

The addition of dyes and/or contrast agents to the crosslinked gel can considerably facilitate the handling of the crosslinked gel during the process of extraction. Thereby, the gel can be localized and visualized at any time during the extraction and the completeness of the extraction can be efficiently verified.

According to a further preferred embodiment of the present invention, the kit additionally comprises a magnet fishing instrument, preferably a magnetic retrieval basket, for removing a magnetic urinary calculus-gel-composite.

Any magnetizable materials can be used for the magnet fishing instrument. These can be coated with a suitable layer, e.g., made of a polymer, for the application. Possible forms of a magnet fishing instrument comprise, e.g., a wire that can be shaped as hooks or loops as well as nets, baskets or pincer-shaped configurations.

A magnet fishing instrument that is suitable for being endoscopically introduced into the body, enables a gentle minimally invasive extraction of the gel. The direct contact between the gel and the fishing instrument leads to magnetic interactions that are strong enough to guarantee a safe extraction.

According to a further preferred embodiment of the present invention, the kit additionally comprises one or several of the constituents selected from the group consisting of application catheter, syringe, mixing cup, mixing syringe and rinsing fluid. The kit according to the invention preferably comprises the constituents that are required for the application in the surgery sterile packed and ready for use for the treatment of a patient. Composition (C) can be mixed with composition (A) or (B) in a mixing cup, preferably in a mixing syringe, before their application. Alternatively, composition (C) can also be injected separately, directly through the application catheter, before the start of the crosslinking The application catheter preferably has a thickness of approx. 1 mm and can be easily inserted through the working channel of a common endoscope.

In the following, the present invention is explained in more detail on the basis of some selected examples.

DETAILED DESCRIPTION

Example 1

Content of a Kit According to the Invention

An exemplary kit according to the invention comprises the following constituents, sterile packed and ready for use:

Composition (A): 10 mL of a 1 g/100 mL alginate solution in water

Composition (B): 10 mL of a water-based chitosan solution (0.32 wt.-%, pH 6) with approx. 15 drops of an oxalic acid solution in water (1 M) as well as 1.5 mL of an aqueous $FeCl_3$ solution (1 M)

Composition (C): 1 mL of a particle suspension in water or in physiological buffer containing 4 to 40 mM iron (0.35 to 3.5 g per liter) (M. Geppert et al., Nanotechnology 22 (2011) 145101).

1 application catheter
1 syringe
1 mixing cup or mixing syringe
1 magnetic retrieval basket (made of PTFE-coated vanadium alloy).

Example 2

Application of a Kit According to the Invention

An aditus to the lumen of the urinary tract (e.g., to the pelvicocaliceal system) is created either ureterorenoscopically (via the urethra, bladder or ureter) or percutaneously (via skin puncture at the flank). A specific port (a metal shaft if applicable) with an inner diameter of 3 to 9 mm is placed therein. An endoscope is inserted into the urinary tract lumen (e.g., into the pelvicocaliceal system) via the created aditus shaft, the surgical area is inspected and the urinary calculus or urinary calculi, respectively, is/are visualized. The urinary calculus or urinary calculi, respectively, is/are smashed by means of a holmium laser. The large and medium sized fragments are removed with the aid of a calculus catching instrument. Compositions (B) and (C) are mixed in a mixing syringe. Subsequently, a catheter is inserted via the endoscopy device (through the aditus) and the mixture of the compositions (B) and (C) according to example 1 is injected into the region of the urinary tract (e.g., into the pelvicocaliceal system) that contains the fragments of the smashed urinary calculus or calculi, respectively.

The catheter is flushed with 0.9% NaCl solution and composition (A) according to example 1 is applied, whereby the gel formation occurs over the course of approx. 1 min. Then a grasping instrument is inserted via the surgical endoscope via the aditus shaft. The solidified gel is grasped in one piece or in several parts with the magnetic retrieval basket and removed from the body via extraction.

The invention claimed is:

1. A kit for producing a crosslinked gel for partly or fully surrounding urinary calculus fragments, the kit comprising:
   (a) a composition (A) comprising one or more cationically crosslinkable polymers,
   (b) a composition (B) comprising one or more crosslinking agents for crosslinking the cationically crosslinkable polymers, and
   (c) a magnetic fishing instrument configured to remove a magnetic urinary calculus-gel-composite by magnetic interaction between the magnetic fishing instrument and the magnetic urinary calculus-gel-composite,
   wherein at least one of composition (A) and composition (B) additionally comprise magnetizable particles or the kit additionally comprises a composition (C) that contains magnetizable particles, wherein the magnetic urinary calculus-gel-composite includes composition (A), composition (B), the magnetizable particles, and urinary calculus fragments.

2. The kit according to claim 1, wherein one or more of the cationically crosslinkable polymers of composition (A) are selected from the group consisting of polysaccharides, polysaccharides with deprotonated or deprotonatable functional groups, carboxy groups, polysaccharides from the group of polyuronides, polysaccharides from the group of alginates and pectins.

3. The kit according to claim 1, wherein one or more of the crosslinking agents of composition (B) are selected from the group consisting of divalent cations, trivalent cations, and iron and calcium ions.

4. The kit according to claim 1, wherein the composition (B) has an acidic pH-value in the range of 3.5 to 4.5.

5. The kit according to claim 1, wherein the magnetizable particles are particles comprising ferromagnetic elements.

6. The kit according to claim 5, wherein the ferromagnetic elements are at least one of iron, nickel cobalt, AlNiCo, SmCo, $Nd_2Fe_{14}B$, $Ni_{80}Fe_{20}$, NiFeCo, $Fe_3O_4$ and $\gamma$-$Fe_2O_3$.

7. The kit according to claim 1, wherein a total amount of the magnetizable particles with regard to the total weight of the compositions (A) or (B) or (C), respectively, that contains the magnetizable particles, is at least 0.1 wt.-%.

8. The kit according to claim 7, wherein the total amount of the magnetizable particles with regard to the total weight of composition (A) or (B) or (C), respectively, that contains the magnetizable particles is in a range of 0.1 to 70 wt.-%.

9. The kit according to claim 1, wherein the concentration of the crosslinking agents that are comprised in the composition (B) is at least 0.1 mol/L.

10. The kit according to claim 9, wherein the concentration of the crosslinking agents that are comprised in composition (B) is in a range of 0.1 to 3 mol/L.

11. The kit according to claim 1, wherein the composition (A), the composition (B), the composition (C) or a composition (D) comprises one or more substances for improving crosslinking of the cationically crosslinkable polymers.

12. The kit according to claim 11, wherein the one or more substances for improving crosslinking of the cationically crosslinkable polymers are amino acids.

13. The kit according to claim 1, wherein the composition (A), the composition (B), the composition (C) or a composition (D) comprised in the kit comprises one or more substances for improving or enabling the formation of covalent bonds between the crosslinked gel and the urinary calculus fragments that are to be partly or fully surrounded.

14. The kit according to claim 1, wherein the composition (A), the composition (B), the composition (C) or a composition (D) comprised in the kit comprises at least one or more further substances from the following list: dyes, contrast agents, preservatives and stabilizers.

15. The kit according to claim 1, wherein the kit additionally comprises one or more constituents selected from the group consisting of application catheter, syringe, mixing cup, mixing syringe and rinsing fluid.

16. The kit according to claim 1, wherein the crosslinked gel is for partly or fully surrounding kidney stone fragments.

17. The kit according to claim 1, wherein the magnetic fishing instrument is a magnetic retrieval basket.

* * * * *